(12) United States Patent
Marino et al.

(10) Patent No.: US 6,280,447 B1
(45) Date of Patent: Aug. 28, 2001

(54) BONY TISSUE RESECTOR

(75) Inventors: James F. Marino, La Jolla; Dan K. Ahlgren, San Diego, both of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/469,727

(22) Filed: Dec. 21, 1999

Related U.S. Application Data (60) Provisional application No. 60/113,651, filed on Dec. 23, 1998.

(51) Int. Cl.[7] .................................................. A61B 17/58

(52) U.S. Cl. .............................. 606/88; 606/80; 606/180; 606/170

(58) Field of Search ................................. 606/80, 88, 78, 606/79, 84, 85, 180, 170, 172, 167, 159

(56) References Cited

U.S. PATENT DOCUMENTS

| | | | |
|---|---|---|---|
| 4,646,738 | | 3/1987 | Trott . |
| 5,720,760 | * | 2/1998 | Becker et al. .................. 606/180 |
| 5,755,718 | * | 5/1998 | Sklar ............................. 606/88 |
| 5,873,886 | * | 2/1999 | Larsen et al. .................. 606/180 |
| 5,913,867 | * | 6/1999 | Dion .............................. 606/180 |
| 5,947,990 | | 9/1999 | Smith . |
| 5,961,532 | * | 10/1999 | Finley et al. ................... 606/170 |
| 5,964,777 | * | 10/1999 | Drucker ......................... 606/180 |

* cited by examiner

Primary Examiner—Pedro Philogene
(74) Attorney, Agent, or Firm—Townsend and Townsend and Crew LLP (57) ABSTRACT

The present invention provides a system for resecting bony tissue such as the facet joint processes using a cannulated resector held by a guidance platform. Rotation of the support holding the cannula causes the resecting surface of a rotating burr to move into contact with the facet joint.

12 Claims, 8 Drawing Sheets

BONY TISSUE RESECTOR

CROSS-REFERENCES TO RELATED APPLICATIONS

The present application is a regular patent application of and claims the benefit of priority from U.S. patent application Ser. No. 60/113,651 filed Dec. 23, 1998, the full disclosure of which is incorporated herein by reference.

TECHNICAL FIELD

The present invention relates to systems for resecting bony tissues.

SUMMARY OF THE INVENTION

The present invention provides a cannulated resector system for resecting a variety of bony tissues. The present invention is ideally suited for resecting the facet joint articular and lateral processes, but may be used to resect any suitable bony tissue.

In an exemplary embodiment, the present cannulated resector is held at a preferred location adjacent the facet joint articular or lateral process by a guidance platform. Rotation of a support which holds a cannula therein causes the cannula to move into contact with the bony tissue to be resected, such that the bony tissue is received within an aperture on the cannula near the distal end of the cannula. A resecting burr, (which is slidably received within the cannula), can then be advanced distally to rescect the bony tissue.

In a preferred aspect, the resector comprises a rotating resecting burr which may be hollow, or have a hollowed out distal end.

The present system is ideally suited for spinal surgery, being particularly well adapted to remove portions of the facet joint such that an operating cannula can be percutaneously positioned with its distal end received within the patient's intervertebral space in a posterolateral approach.

BEST MODES OF CARRYING OUT THE INVENTION

Figure 1:
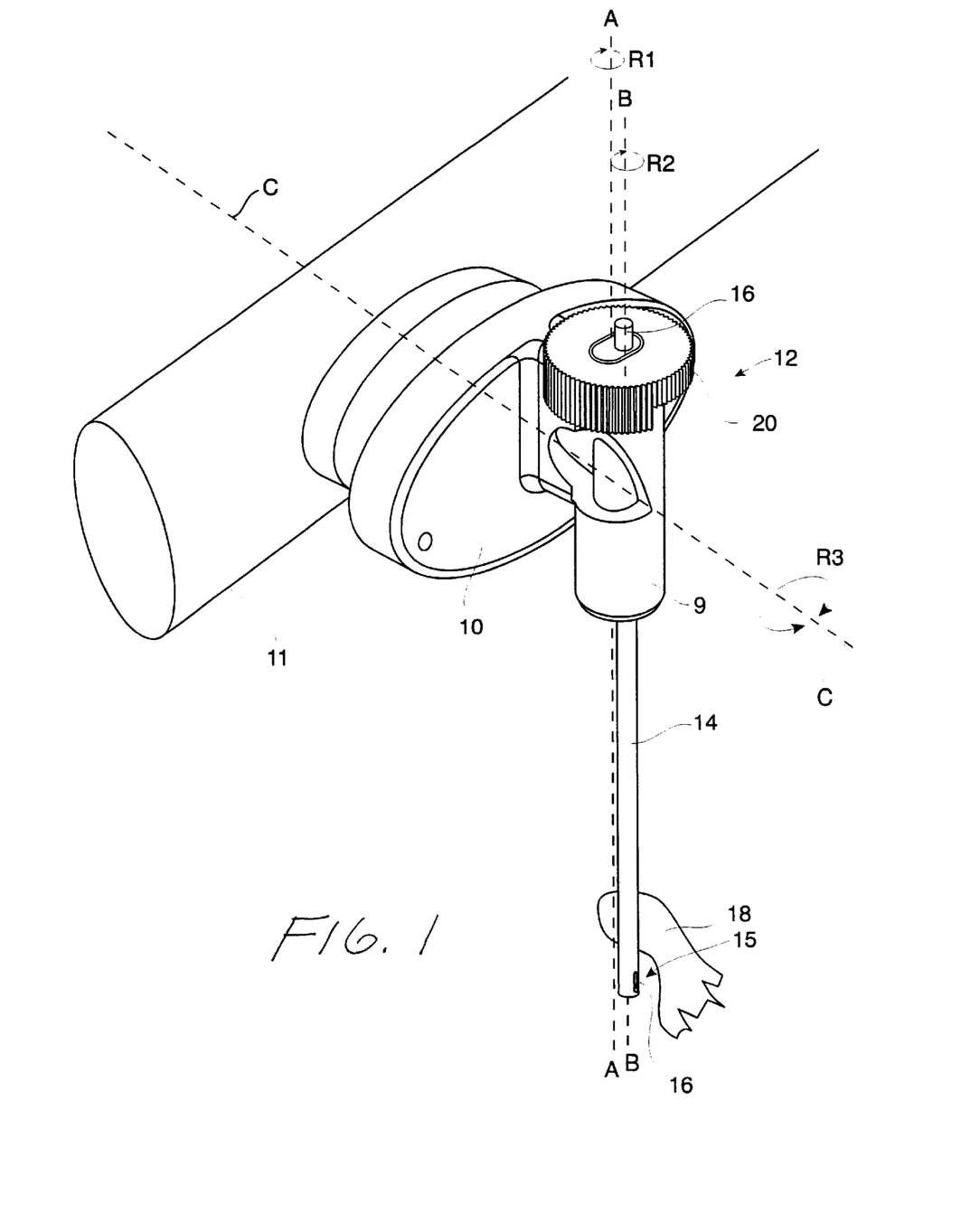
FIG. 1 is a perspective view of the present invention.

FIG. 1 shows a perspective view of the present invention. A cannula guide 10 is preferably mounted to a fixed guidance platform crossbeam 11, or to any suitable cannula positioning arm which is positioned over or above a patient. A suitable guidance platform and cannula guide for use with the present invention is fully disclosed in provisional U.S. patent application Ser. No. 60/113,651 and in regular U.S. patent application Ser. No. 09/326,739, in which cannula guide 10 is pivotally mounted to guidance platform crossbeam 11 such that cannula guide 10, (and cannula 14 which is held by support 10), can be rotated in direction R3 about axis C.

A cannula positioning system 12 is used to suspend cannula 14 and to move cannula 14 such that rotating resecting burr 16 can be positioned in contact with the bony tissue to be resected, as will be explained.

In the following illustrations, the bony tissue to be resected comprises a facet joint 18, however, the present invention is not so limited, as other suitable bony tissues may be resected.

Figure 2:
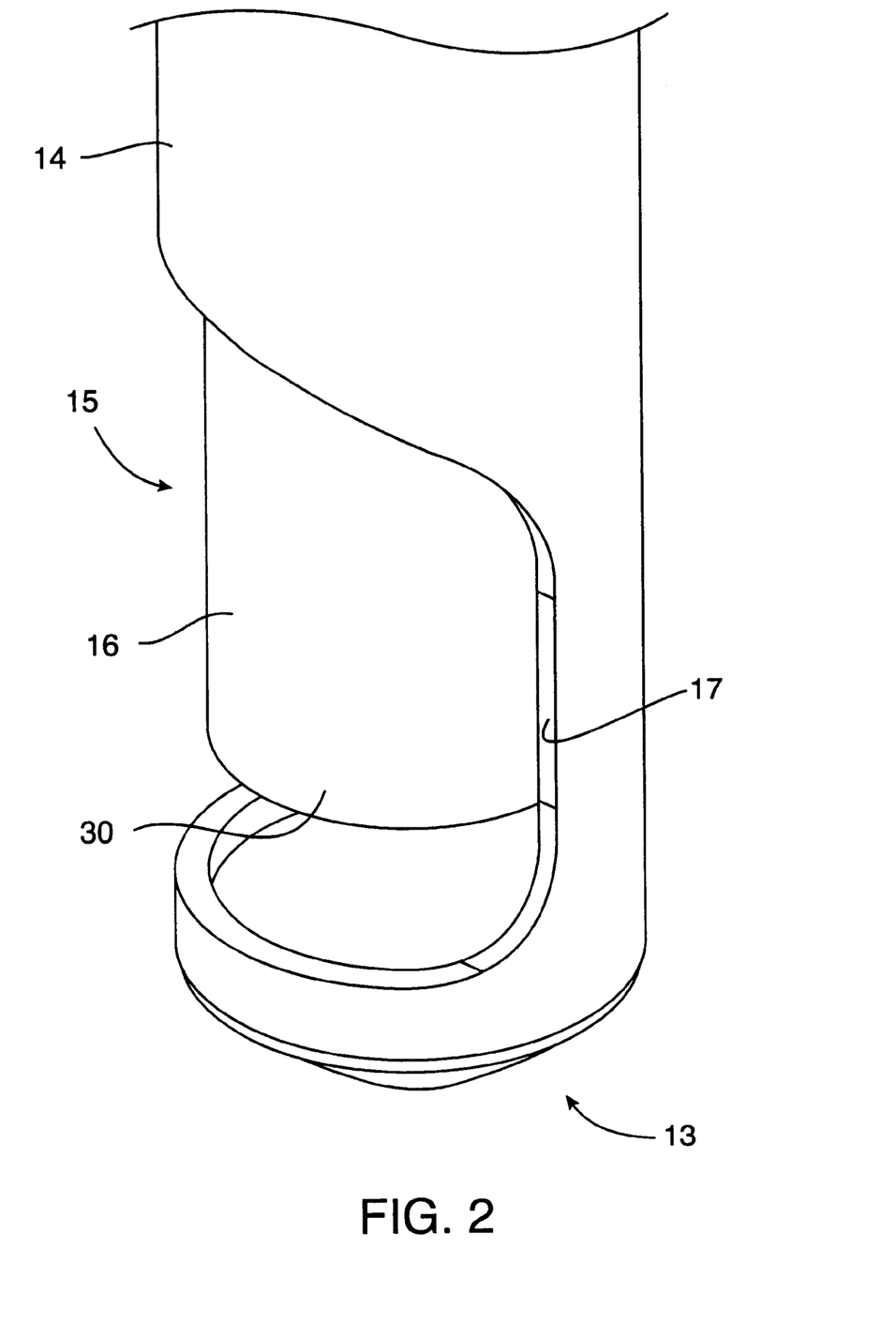
FIG. 2 is a perspective view of the distal tip of a cannula showing a window in the cannula through which a resecting burr is exposed.

Cannula 14 has a small window 15 positioned near its distal end (the details of which are best seen in FIG. 2). Rotating resecting burr 16 is received within cannula 14 and can be distally advanced to resect bony tissue, (for example, facet joint 18), after a portion of facet joint 18 is received into cannula 12 through window 15. The rotation of resecting burr 16 will grind against facet joint 18 such that facet joint 18 is thereby resected. Specifically, the rotation of burr 16 around axis B in direction R2 will cause burr 16 to grind against facet joint 18, thereby resecting it. An optional motorized mechanism (not shown) can be provided to cause burr 16 to rotate about axis B. Alternatively, a gripping attachment can be provided such that burr 16 may be rotated by hand.

The resection of facet joint 18 is advantageous in providing a suitably large cannula opening for minimally invasive spinal procedures, and in particular in providing an open path for the insertion of an operating cannula in a posterolateral approach into the patient's intervertebral space.

Figure 3:
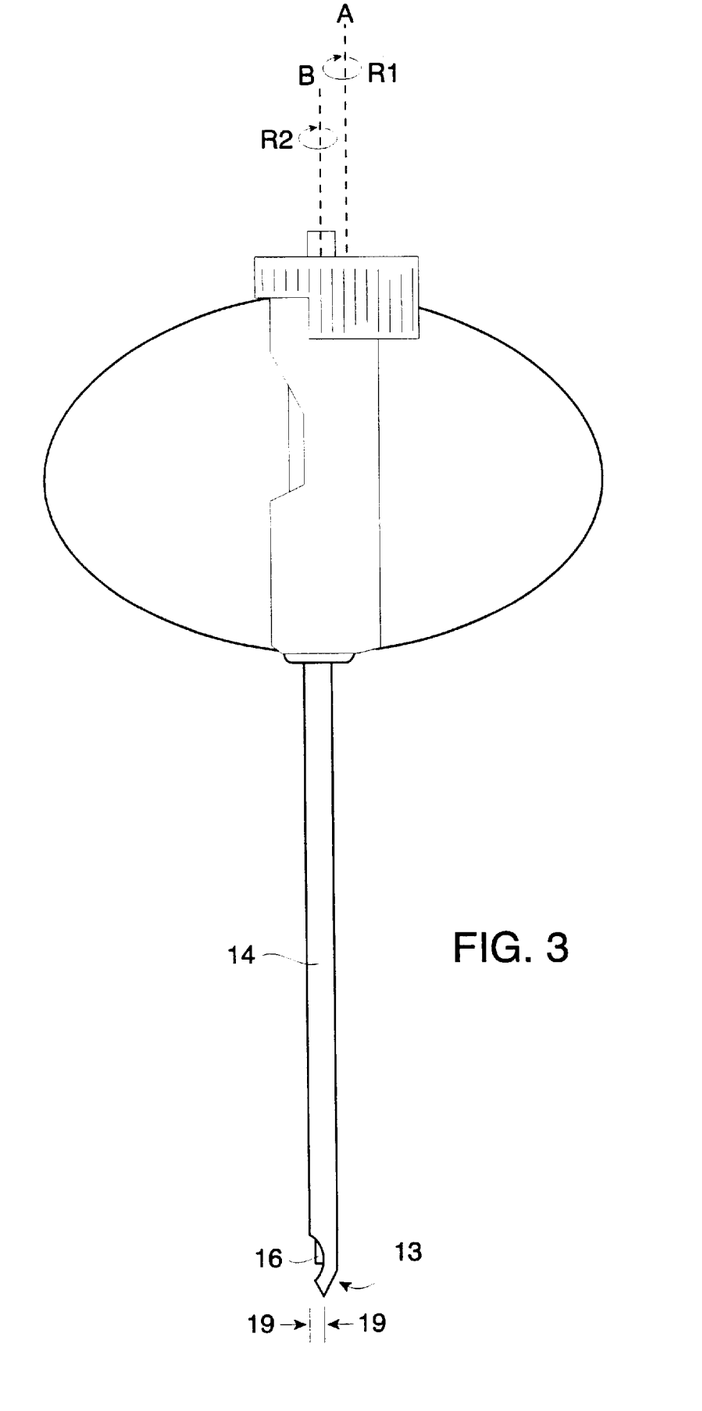
FIG. 3 is a side elevation view of the present invention.
Figure 4:
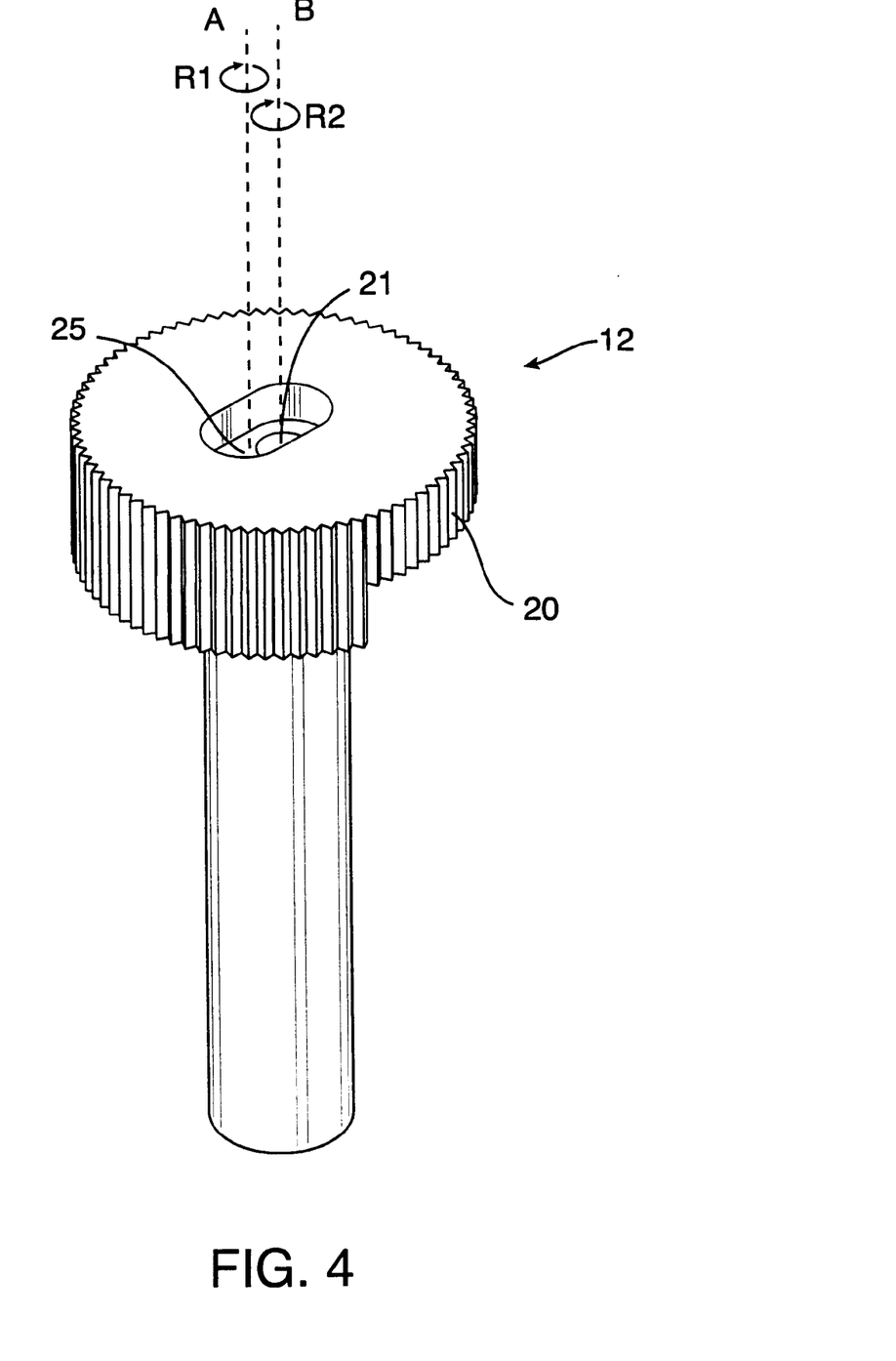
FIG. 4 is a perspective view of a cannula positioning system for moving the cannula to a position adjacent the tissue to be resected.

As is shown in FIG. 2, sides 17 of window 15 of cannula 14 will operate to prevent excessive resection of the facet joint. Prior to resection, cannula 14 is positioned such that the edges of facet joint 18 will abut against sides 17 of window 15. Burr 16 can then be advanced downwardly (ie: distally) through cannula 14 thereby cutting into and resecting the facet joint. Accordingly, as is shown in FIG. 3, a resection distance 19 will be achieved, with the portion of facet joint 18 (or other bony tissue), received in cannula 12 through window 15 being resected.

Subsequent to resection, burr 16 can then be retracted, allowing the facet joint to be recaptured within window 15. Burr 16 can then be again advanced downwardly (ie: distally) in cannula 14 to resect facet joint 18. This creates a milling action which may utilize the optional conical distal end 30 of burr 16, (see FIG. 6), to control drift of burr 16 on the facet joint, as will be explained below.

It is to be understood that by dimensioning window 15 with a larger or smaller opening (as defined by the relative positioning of edges 17), greater or smaller amounts of maximum facet resection can be achieved. It is also seen in FIG. 3, distal end 13 of cannula 14 is preferably tapered to provide protection when distal end 13 of cannula 14 is initially inserted into the patient, for example, to locations proximal the articular process. Being closed, end 13 of cannula 14 can advantageously be positioned below the bony tissue to be resected such that the tissues "below" (ie: positioned distal to), the bony tissue to be resected are protected from the cutting action of rotating resecting burr 16. As such, tapered closed end 13 of cannula 14 may prevent the distal end 21 of burr 16 from contacting sensitive tissues below the articular process. Moreover, tapered end 13 facilitates soft tissue penetration, as tapered end 13 will also minimize tissue damage when cannula 14 is initially inserted into the patient.

Figure 6:
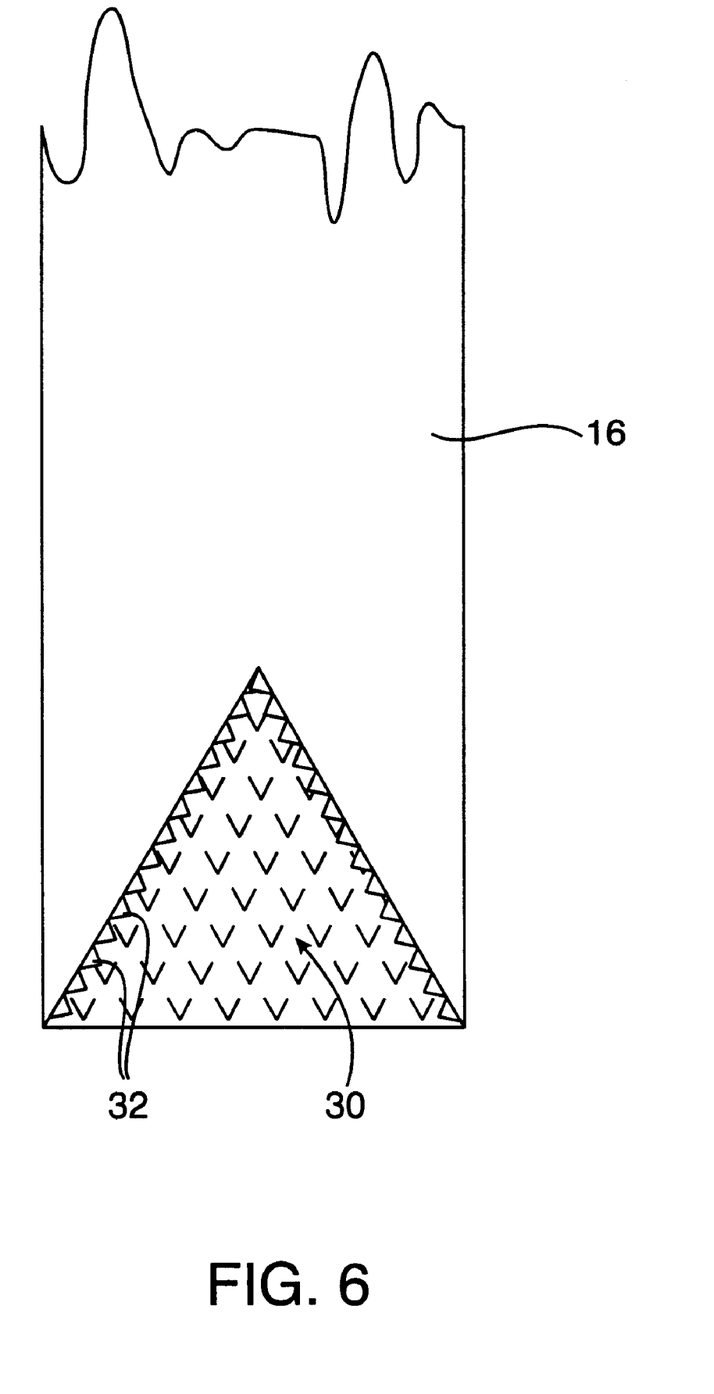
FIG. 6 is a sectional view of the distal end of a rotating resecting burr.

FIG. 6 shows a sectional view of an optional hollowed out conical distal end tip 30 of burr 16. End tip 30 may comprise teeth 32, (or other suitable protrusions), for cutting through and thereby resecting the facet joint. The inverted conical shape of end 30 of burr 16 ensures that burr 16 is self-centering on the facet joint, thereby preventing the burr from "walking" on the surface of the joint as it is rotated. A further advantage of the inverted conical shape of end 30 is that as the facet joint is resected, cut away bone fragments may be stored within the conical shape of end tip 30. Such bone fragments can later be extracted and then be deposited onto bleeding bone surfaces to minimize subsequent bleeding, or to promote bone growth. Alternatively, burr 16 may be fully hollowed out, either at its distal end, or along its entire length, so as to trap bone fragments in its hollowed out interior.

In an alternative aspect of the present invention, distal tip 13 of cannula 14 is removable such that cut away bone fragment material stored within conical end 30 can be removed from distal end 13 of cannula 14 after use.

Referring to FIGS. 1, 3, 4, and 5, an exemplary embodiment of cannula positioning system 12 is shown. In this aspect, cannula positioning system 12 comprises an elongated rotating knob 20 having a hole 21 passing therethrough, in which cannula 14 is suspended. Burr 16 is then inserted through hole 23 in cannula 14 such that distal end 30 projects downwardly into window 15.

Figure 5:
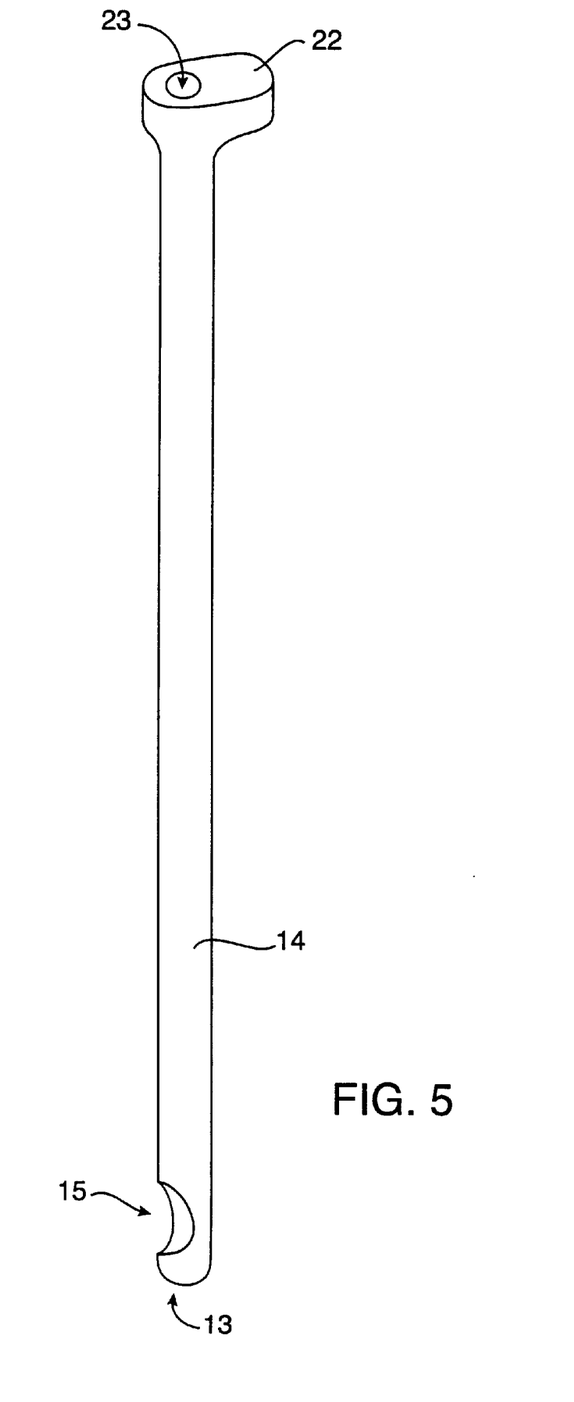
FIG. 5 is a perspective view of the cannula.

As is seen in FIG. 5, an extending support portion 22 is provided at the distal end of cannula 14. Extending support portion 22 is received into recession 25 (FIG. 4) when cannula 14 is suspended therein such that cannula 14 is supported in hole 21 and prevented from rotating with respect to knob 20. Rotating knob 20 rotates around axis A. Burr 16 rotates about axis B. Axis B is parallel to axis A, as shown. Therefore, as knob 20 is rotated about axis A in direction R1, axis B will move around axis A in direction R1, such that cannula 14 and burr 16 can be moved into contact with facet joint 18.

Figures 7, 8:
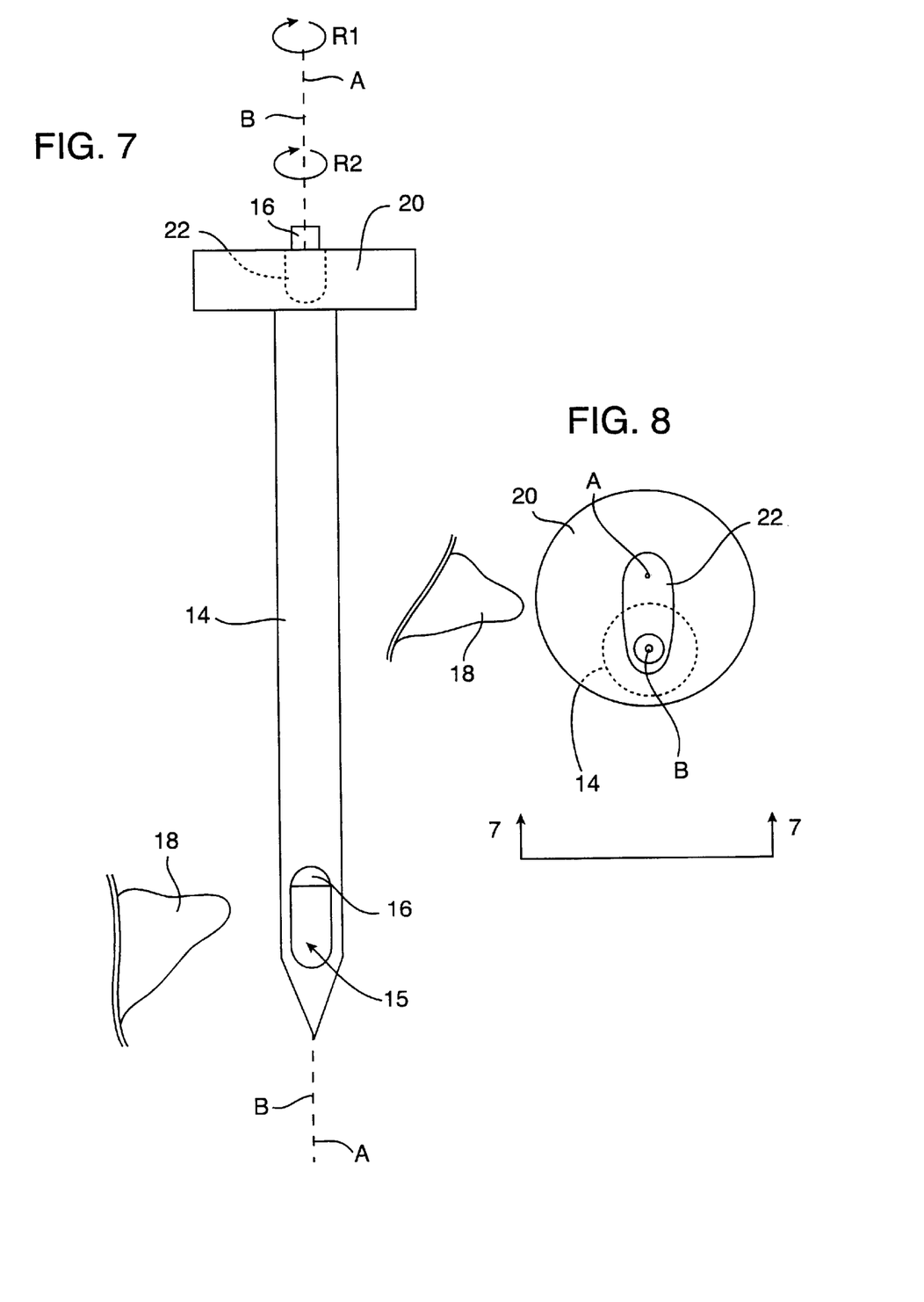
FIG. 7 is a side elevation view of the cannula positioning system in a first position (taken along line 7—7 in FIG. 8).
FIG. 8 is an top view corresponding to FIG. 7.

Further details of the operation of cannula positioning system 12 are seen in FIGS. 7 and 8. Referring to FIG. 7, cannula 14 is initially positioned such that it is suspended near facet joint 18. FIG. 8 shows a top view corresponding to FIG. 7 with cannula 14 in a first position.

Figure 9:
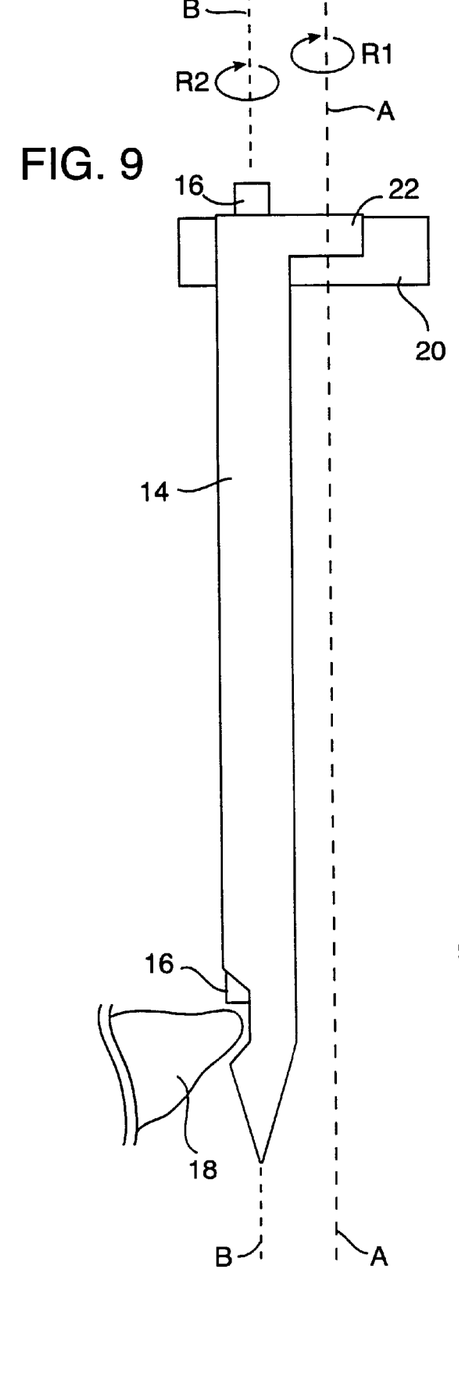
FIG. 9 is a side elevation view of the cannula positioning system in a second position (taken along line 9—9 in FIG. 10).
Figure 10:
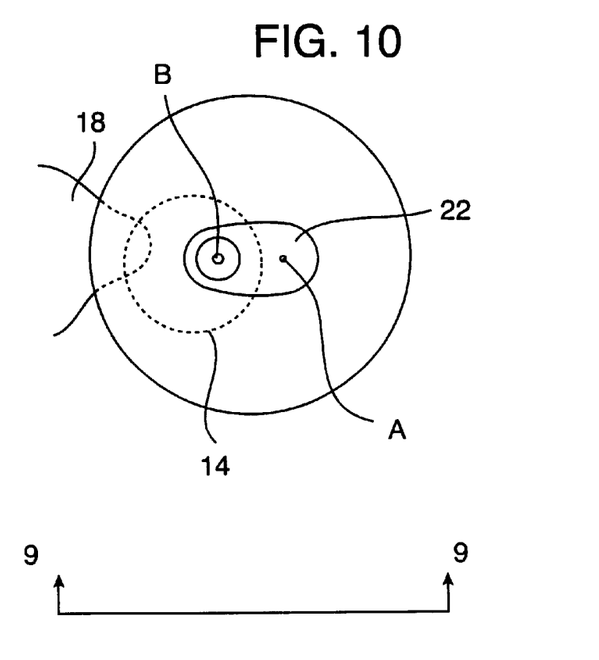
FIG. 10 is an top view corresponding to FIG. 9.

FIGS. 9 and 10 show the cannula moved to a second position after knob 20 has been rotated by 90°. As can be seen, a portion of facet joint 18 is received within aperture 15 such that rotating resecting burr 16 can then be distally advanced to resect facet joint 18.

In this embodiment, cannula positioning system 12, (ie: knob 20 with cannula 14 supported therethrough), moves cannula 14 such that from a first position to a second position, wherein cannula 14 points in the same direction at each of the first and second positions (ie: the orientation of cannula 14 in FIGS. 7 and 8 is parallel to the orientation of cannula 14 in FIGS. 9 and 10).

The relative position of window 15 can be determined simply by viewing the relative position of extending support 22 within handle 20. As such, the surgeon is able to rotate handle 20, knowing where burr 16 will contact facet joint 18 through window 15.

What is claimed is:

1. A bony tissue resecting system, comprising:
   a cannula having a side aperture near its distal end; and
   a rotatable resecting element received within the cannula the rotatable resecting element having a hollowed out distal end.

2. The bony tissue resecting system of claim 1, wherein, the rotatable resecting element can be distally advanced within the cannula.

3. The bony tissue resecting system of claim 1, further comprising:
   a cannula positioning system adapted to move the cannula from a first position to a second position, wherein the cannula points in the same direction at each of the first and second positions.

4. The bony tissue resecting system of claim 1, further comprising:
   a cannula positioning system adapted to move the cannula from a first position to a second position, wherein the orientation of the cannula in the first position is parallel to the orientation of the cannula in the second position.

5. The bony tissue resecting system of claim 4, wherein the cannula positioning system comprises:
   a support which is rotatable about a central axis, wherein the support holds the cannula in an orientation such that the central longitudinally extending axis of the cannula is parallel to the central axis of the support.

6. The bony tissue resecting system of claim 1, wherein, the cannula has an enclosed tapered end.

7. A method of resecting a portion of a bony tissue joint, comprising:
   positioning a cannula adjacent a bony tissue joint such that a portion of the bony tissue joint is received within a side aperture in the cannula, wherein the side aperture is disposed near the distal end of the cannula; and
   distally advancing a rotatable resecting element through the cannula such that the rotatable resecting element resects the portion of the bony tissue joint received within the side aperture of the cannula, wherein the rotatable resecting element has a hollowed out distal end, and wherein the portion of the bony tissue resected is received within the hollowed out distal end.

8. The method of claim 7, wherein, the cannula is positioned adjacent the bony tissue joint by rotating a cannula support about a central axis, wherein the cannula support holds the cannula such that the central longitudinally extending axis of the cannula is parallel to the central axis of the cannula support.

9. The method of claim 7, wherein, the rotatable resecting element is advanced distally such that tissue resected from the bony tissue joint is received within a hollowed out distal end of the rotatable resecting element.

10. The method of claim 7, wherein, the rotatable resecting element is advanced distally such that tissue resected from the bony tissue joint is received between a closed distal end of the cannula and the distal end of the rotatable resecting element.

11. A bony tissue resecting system, comprising:
   a cannula having a side aperture near its distal end;
   a rotatable resecting element received within the cannula; and
   a cannula positioning system adapted to move the cannula from a first position to a second position, wherein the orientation of the cannula in the first position is parallel to the orientation of the cannula in the second position, and wherein the cannula positioning system comprises:

a support which is rotatable about a central axis, wherein the support holds the cannula in an orientation such that the central longitudinally extending axis of the cannula is parallel to the central axis of the support.

12. A method of resecting a portion of a bony tissue joint, comprising:

positioning a cannula adjacent a bony tissue joint such that a portion of the bony tissue joint is received within a side aperture in the cannula, wherein the side aperture is disposed near the distal end of the cannula; and distally advancing a rotatable resecting element through the cannula such that the rotatable resecting element resects the portion of the bony tissue joint received within the side aperture of the cannula, wherein the cannula is positioned adjacent the bony tissue joint by rotating a cannula support about a central axis, wherein the cannula support holds the cannula such that the central longitudinally extending axis of the cannula is parallel to the central axis of the cannula support.

* * * * *